United States Patent [19]
Fell et al.

[11] Patent Number: 5,204,244
[45] Date of Patent: Apr. 20, 1993

[54] PRODUCTION OF CHIMERIC ANTIBODIES BY HOMOLOGOUS RECOMBINATION

[75] Inventors: H. Perry Fell, Redmond; Kim R. Folger Bruce, Seattle, both of Wash.

[73] Assignee: Oncogen, Seattle, Wash.

[21] Appl. No.: 243,873

[22] Filed: Sep. 14, 1988

Related U.S. Application Data

[63] Continuation-in-part of Ser. No. 113,800, Oct. 27, 1987, abandoned.

[51] Int. Cl.$^5$ .................. C12N 15/00; C12N 5/00
[52] U.S. Cl. ....................... 435/69.6; 435/172.3; 435/240.2; 435/240.26; 435/240.27; 435/320.1; 435/69.1; 530/387.3; 530/388.85; 935/70; 935/15
[58] Field of Search .............. 435/68, 172.3, 240.2, 435/240.26, 240.27, 320, 69.1, 69.6; 530/387

[56] References Cited

PUBLICATIONS

Neuberger et al. (a), PCT/GB85/00392 (WO86/01533) Mar. 1986.
Neuberger et al. (b) Nature 312:604 (1984).
Morrison, Science 229: 1202-1207 (1985).
Smithies et al., Nature 317: 230-234 (1985).
Hellström et al., Cancer Res. 46: 3917-3923 (1986).
Boulianne et al., Nature 312: 643-646 (1984).
Thomas et al., Cell 44: 419-428 (1986).
ATCC Catalog, 6th edition, 1988, p. 326 and p. 327.
Doetschman et al., Nature 330: 576-578 (1987).
Hohmann et al., 1987, Curr. Genet. 12: 519-526.
Folger et al., 1985, Mol. Cell. Biol. 5: 59-69.
Lin et al., 1985, Proc. Natl. Acad. Sci. 82: 1391-1395.
Roth et al., 1985, Proc. Natl. Acad. Sci. 82: 3355-3359.
Shaul et al., 1985, Proc. Natl. Acad. Sci. 82: 3781-3784.
Anderson et al., 1984, Proc. Natl. Acad. Sci. 81: 206-210.
Bandyopadhyay et al., 1984, Proc. Natl. Acad. Sci. 81: 3476-3480.
Folger et al., 1984, Cold Spring Harbor Symp. Quiant. Biol. 49: 123-138.
Katinka, 1984, Biochimie 66: 681-692.
Kucherlapati et al., 1984, Proc. Natl. Acad. Sci. 81: 3153-3157.
Lin et al., 1984, Mol. Cell. Biol. 4: 1020-1034.
Goodenon et al., 1983, Nature 301: 388-394.
Subramani et al., 1983, Mol. Cell. Biol. 3: 1040-1052.
Folger et al., 1982, Mol. Cell. Biol. 2: 1372-1387.
EPA, 0173494, Morrison et al., publ. Mar. 5, 1986.
Morrison et al., 1984, Proc. Natl. Acad. Sci. 81: 6851-6855.
Robins et al., 1981, Cell 23: 29-39.
Baker et al., Sep. 1988, Proc. Natl. Acad. Sci. USA 85: 6432-6436.

*Primary Examiner*—Elizabeth C. Weimar
*Assistant Examiner*—Jasemine C. Chambers
*Attorney, Agent, or Firm*—Pennie & Edmonds

[57] ABSTRACT

A process for producing chimeric antibodies using novel recombinant DNA vectors and homologous recombination in vivo is described. The recombinant DNA constructs of the invention can be used to transfect antibody producing cells so that targeted homologous recombination occurs in the transfected cells leading to gene modification and the production of chimeric antibody molecules by the transfected cells.

21 Claims, 6 Drawing Sheets

FIG. 1 (Con't) C

PRODUCTION OF CHIMERIC ANTIBODIES BY HOMOLOGOUS RECOMBINATION

The present application is a continuation in part of copending application Ser. No. 113,800, filed Oct. 27, 1987, now abandoned, which is incorporated herein in its entirety.

TABLE OF CONTENTS

1. Introduction
2. Background of the Invention
   2.1. Chimeric Antibodies
   2.2. Homologous Recombination
3. Summary of the Invention
   3.1. Definitions
4. Description of the Figures
5. Detailed Description of the Invention
   5.1. Target Vectors
      5.1.1 Target Sequence
      5.1.2. Replacement Gene
      5.1.3. Selectable Marker and Other Elements
   5.2. Transfection of Antibody-Producing Cell Lines
   5.3. Screening and Selection of Recombinants
6. Example: Replacement of the Constant Region of a Murine Immunoglobulin Heavy Chain with the Constant Region of Human Gamma 1 Immunoglobulin
   6.1. Materials and Methods
      6.1.1. Transfection
      6.1.2. Screening Transfectants for Successful Recombinants
      6.1.3. Southern and Western Blots
   6.2. Construction of Target Plasmids Encoding Human Immunoglobulin Constant Region
   6.3. Transfection and Homologous Recombination
      6.3.1. Co-Transfection of Murine Myeloma Cells
      6.3.2. Identification of Cells Secreting Chimeric Immunoglobulins
7. Example: Production of Chimeric Immunoglobulin Heavy Chain with Specificity to L20 Human Tumor Associated Antigen
   7.1. Construction of Target Vector and Transfection of Hybridoma L20
   7.2. Characterization of Expressed Chimeric L20 Heavy Chain
      7.2.1. Western Blot Analysis
      7.2.2. Flow Cytometric Analysis
      7.2.3. Southern Blot Analysis
      7.2.4. ADCC Analysis
   7.3. Chimeric L20 Heavy Chain Produced Using a Different Target Vector
8. Construction of Chimeric G28.1 Heavy Chains
9. Construction of Chimeric L6 Heavy Chains

INTRODUCTION

The present invention relates to a process for producing chimeric antibodies using novel recombinant DNA vectors and homologous recombination in situ. The recombinant DNA constructs of the invention can be used to transfect antibody producing cells so that targeted homologous recombination occurs in the transfected cells leading to the production of chimeric antibody molecules by the transfected cells.

The invention is demonstrated by way of examples described in which the constant regions of a murine immunoglobulin heavy chain were replaced by human IgG1 constant regions and chimeric heavy chains were produced by the murine cell line.

2. BACKGROUND OF THE INVENTION

2.1. Chimeric Antibodies

Since the development of the cell fusion technique for the production of monoclonal antibodies (Kohler and Milstein, 1975, Nature (London) 256:495) a vast number of monoclonal antibodies, many of which define heretofore unknown antigens, have been produced by a number of researchers. Unfortunately, most of the monoclonal antibodies made to date are produced in a murine system and, therefore, have limited utility as human therapeutic agents unless modified in some way so that the murine monoclonal antibodies are not "recognized" as foreign epitopes and "neutralized" by the human immune system. A number of researchers, therefore, are attempting to develop human monoclonal antibodies, which are "recognized" less well as foreign epitopes and may overcome the problems associated with the use of monoclonal antibodies in humans. Obviously, the hybridoma technique developed by Kohler and Milstein (supra) which involves sacrificing the immunized mice and using their spleens as a source of lymphocytes for subsequent fusion to immortalize antibody producing cell lines cannot be practiced in humans. Therefore, a number of researchers have directed their attention to recent advances in the field of molecular biology that allow for the introduction of DNA into mammalian cells to obtain expression of immunoglobulin genes (Oi et al., 1983 Proc. Natl. Acad. Sci. USA 80:825; Potter et al., 1984, Proc. Natl. Acad. Sci. USA 81:7161), and have used these techniques to produce chimeric antibodies (Morrison et al., 1984, Proc. Natl. Acad. Sci. USA 81:6581; Sahagan et al. 1986, J. Immunol. 137:1066; Sun et al., 1987, Proc. Natl. Acad. Sci. 84:214).

Chimeric antibodies are immunoglobulin molecules comprising a human and non-human portion. More specifically, the antigen combining region (or variable region) of a chimeric antibody is derived from a non-human source (e.g., murine) and the constant region of the chimeric antibody (which confers biological effector function to the immunoglobulin) is derived from a human source. The chimeric antibody should have the antigen binding specificity of the non-human antibody molecule and the effector function conferred by the human antibody molecule.

In general, the procedures used to produce these chimeric antibodies consist of the following steps (the order of some steps may be interchanged):

(a) identifying and cloning the correct gene segment encoding the antigen binding portion of the antibody molecule; this gene segment (known as the VDJ, variable, diversity and joining regions for heavy chains or VJ, variable, joining regions for light chains (or simply as the V or Variable region) may be in either the cDNA or genomic form;

(b) cloning the gene segments encoding the constant region or desired part thereof;

(c) ligating the variable region with the constant region so that the complete chimeric antibody is encoded in a transcribable and translatable form;

(d) ligating this construct into a vector containing a selectable marker and gene control regions such as promoters, enhancers and poly(A) addition signals;

(e) amplifying this construct in bacteria;

(f) introducing the DNA into eukaryotic cells (transfection) most often mammalian lymphocytes;

(g) selecting for cells expressing the selectable marker;

(h) screening for cells expressing the desired chimeric antibody; and (i) testing the antibody for appropriate binding specificity and effector functions.

Antibodies of several distinct antigen binding specificities have been manipulated by these protocols to produce chimeric proteins (e.g., anti-TNP: Boulianne et al., 1984, Nature Vol. 312 pg. 643; and anti-tumor antigens: Sahagan et al., 1986, J. Immunol. Vol. 137:1066). Likewise several different effector functions have been achieved by linking new sequences to those encoding the antigen binding region. Some of these include enzymes (Neuberger et al., 1984, Nature 312:604), immunoglobulin constant regions from another species and constant regions of another immunoglobulin chain (Sharon et al., 1984, Nature 309:364; Tan et al., 1985, J. Immunol. Vol. 135:3565-3567).

2.2. Homologous Recombination

Another recent advance in the field of molecular biology is the discovery that cultured mammalian cells will integrate exogenous plasmid DNA into chromosomal DNA at the chromosome location which contains sequences homologous to the plasmid sequences. This event is referred to as homologous recombination (Folger, et al. 1982, Mol. Cell. Biol. 2, 1372-1387; Folger, et al., 1984, Symp. Quant. Biol 49, 123-138; Kucherlapati, et al., 1984, Proc. Natl. Acad. Sci. USA 81, 3153-3157; Lin, et al., 1985, Proc. Natl. Acad. Sci. USA 82, 1391-1395; Robert de Saint Vincent, et al., 1983, Proc. Natl. Acad. Sci. USA 80, 2002-2006; Shaul, et al., 1985, Proc. Natl. Acad. Sci. USA 82, 3781-3784). Mammalian cells also contain the enzymatic machinery to integrate plasmid DNA at random chromosomal sites, referred to as nonhomologous recombinations. The frequency of homologous recombination has been reported to be as high as between 1/100 to 1/1000 of the recombinational events, while the majority of recombinations result from nonhomologous interactions (Thomas et al., 1986, Cell 44:419-428; Smithies et al., 1985, Nature 317:230-234; Shaul, et al., 1985, Proc. Natl. Acad. Sci. USA 82, 3781-3784; Smith, et al., 1984, Symp. Quant. Biol. 49, 171-181; Subramani, et al., 1983, Mol. Cell. Biol. 3, 1040-1052). The existence of the cell machinery for homologous recombination makes it possible to modify endogenous genes in situ. In some instances, conditions have been found where the chromosomal sequence can be modified by introducing into the cell a plasmid DNA which contains a segment of DNA homologous to the target locus and a segment of new sequences with the desired modification (Thomas et al., 1986, Cell 44:419-428; Smithies et al., 1985, Nature 317:230-234; Smith, et al., 1984, Symp. Quant. Biol. 49, 171-181). Homologous recombination between mammalian cell chromosomal DNA and the exogenous plasmid DNA can result in the integration of the plasmid or in the replacement of some of the chromosomal sequences with homologous plasmid sequences. The process of replacing homologous DNA sequences is referred to as gene conversion. Both the integration and the conversion events can result in positioning the desired new sequence at the endogenous target locus.

However, the process of homologous recombination has mostly been studied using genes which offer dominant selection such as NEO and HPRT and only for a very few cell types (Song et al., 1987, Proc. Natl. Acad. Sci. USA 84:6820-6824; Rubinitz and Subramani, 1986, Mol. Cell Biol. 6:1608-1614; and Liskay, 1983, Cell 35:157-164). It has not been determined whether or not lymphocytes or myeloma cells are capable of mediating such events or whether immunoglobulin genes could be usefully targeted or reconstructed by such a process.

3. SUMMARY OF THE INVENTION

The present invention is directed to a process for modifying antibody molecules and for creating and producing chimeric antibody molecules in which the antigen combining region is linked (a) to an immunoglobulin constant region or some portion thereof, that confers a desired characteristic such as effector function, class (e.g., IgG, IgA, IgM, IgD or IgE) origin (e.g., human or other species); or (b) to another type of molecule conferring some other function to the chimeric antibody molecule (e.g., an enzyme, toxin, a biologically active peptide, growth factor inhibitor, or linker peptide to facilitate conjugation to a drug, toxin, or other molecule, etc.).

The invention uses novel recombinant DNA vectors to engineer targeted gene modification accomplished via homologous recombination, in either (a) cell lines that produce antibodies having desired antigen specificities, so that the antigen combining site of an antibody molecule remains unchanged, but the constant region of the antibody molecule, or a portion thereof, is replaced or altered; or (b) cell lines that produce antibodies of desired classes which may demonstrate desired effector functions, so that the constant region of an antibody molecule remains unchanged, but the variable region of the antibody molecule or a portion thereof, is replaced or altered.

According to one embodiment of the invention, a novel recombinant DNA vector is used to transfect a cell line that produces an antibody having a desired antigen specificity. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" which allows for homologous recombination and targeted gene conversion within the antibody producing cell. In an alternate embodiment of the invention, a novel DNA vector is used to transfect a cell line that produces an antibody having a desired effector function, in which case, the replacement gene contained in the novel recombinant vector may encode all or a portion of a region of an antibody molecule having a desired antigen specificity, and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc. Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA which encodes a modification for a monoclonal antibody can be targeted directly to the site of the expressed immunoglobulin gene within a B-cell or hybridoma cell line. DNA constructs for any particular modification may be used to alter the protein product of any monoclonal cell line or hybridoma. Such a procedure circumvents the costly and time consuming task of cloning both heavy and light chain variable region genes from each B-cell clone expressing a useful antigen specificity. In addition to circumventing the process of cloning variable region genes, the level of expression of chimeric antibody should be higher when the gene is at its natural chromosomal location rather than at a random position.

3.1 Definitions

The following terms, as used herein, whether in the singular or plural, shall have the meanings indicated:

Chimeric Antibody: an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Replacement Gene: a gene that encodes a product to replace all or a portion of either the constant region or variable region of an antibody molecule to form a chimeric antibody molecule. Replacement genes are constructed into novel recombinant DNA target vectors of the invention which are used to transfect antibody-producing cell lines. For the modification of all or a portion of a constant region, replacement genes of the invention may include, but are not limited to an immunoglobulin constant region having a particular effector function, class and/or origin (e.g., IgG, IgA, IgM, IgD, or IgE constant regions of human immunoglobulins or any other species) or a portion of a constant region which modifies the activity or properties of the constant region of the immunoglobulin; as well as genes which encode other molecules that confer some new function to a chimeric antibody molecule, e.g., an enzyme, toxin, hormone, growth factor, conjugatable linker, etc. For the modification of all or a portion of a variable region, replacement genes of the invention may include, but are not limited to immunoglobulin variable regions that encode a different variable region having a different antigen affinity or specificity, or a portion of a variable region which modifies the activity or properties of the variable region of the immunoglobulin so that the resulting chimeric antibody has a greater affinity or higher degree of specificity for the antigen.

Target Sequence: a sequence homologous to DNA sequences that flank or occur adjacent to the region to be converted of an antibody molecule in the chromosome of a cell that produces the antibody molecule. Target sequences are constructed into novel recombinant DNA vectors of the invention which are used to transfect antibody-producing cell lines.

Target sequences for heavy chain recombinations that direct replacement of or insertion within all or a portion of the constant region may include but are not limited to all or a portion of the V, D, J, and switch region (including intervening sequences called introns) and flanking sequences associated with or adjacent to the particular heavy chain constant region gene expressed by the antibody producing cell line to be transfected and may include regions located within or downstream of the constant region (including introns). Target sequences for light chain recombinations that direct replacement of or insertion within all or a portion of the constant region may include but are not limited to the V and J regions, their upstream flanking sequences, and intervening sequences (introns), associated with or adjacent to the light chain constant region gene expressed by the antibody producing cell line to be transfected and may include regions located within or downstream of the constant region (including introns).

Target sequences for heavy chain recombinations that direct replacement of or insertion within all or a portion of the variable region may include but are not limited to all or a portion of the V, D, and J regions (including introns) and flanking sequences associated with or adjacent to the particular variable region gene expressed by the antibody producing cell line to be transfected. Target sequences for light chain recombinations that direct replacement of or insertion within all or a portion of the variable region may include but are not limited to the V and J region (including introns) and flanking sequences associated with or adjacent to the light chain variable region gene expressed by the antibody producing cell line to be transfected.

Target Vector: a recombinant nucleotide vector comprising a target sequence and a replacement gene which can be used to engineer the production of chimeric antibodies by antibody-producing cells transfected with the target vector. The target vectors are used to transfect cell lines that contain sequence(s) homologous to the vector's target sequence and produce an antibody having (a) a desired antigen specificity; (b) a desired constant region; or (c) another desired quality such as high secretion levels, large scale culture adaptability, etc.

The following abbreviations shall have the meanings shown below:
FITC: fluorescein isothiocyanate
HRP: horseradish peroxidase
hu: human
huC$\gamma$1: constant region exons of human gamma immunoglobulin 1
huIgG: human gamma immunoglobulin
m: mouse
mAB: monoclonal antibody
mIgG: mouse gamma immunoglobulin

4. DESCRIPTION OF THE FIGURES

FIG. 1 diagrammatically represents a generalized scheme for gene replacement via homologous recombination using the target vectors of the invention. Variable (V), diversity (D), joining (J), switch (S) and constant (C) regions are indicated. Panel A schematically represents the replacement of all or a portion of the constant or variable region of the heavy chain genes using a target sequence homologous to any portion spanning the V, D, J, S, and C region. Panel B schematically represents the replacement of all or a portion of the constant or variable region of the light chain genes using a target sequence homologous to any portion spanning the V, J, and C region. Panel C schematically represents the replacement of all or a portion of the variable or constant regions in either light or heavy chain genes using sequences that flank the gene to be replaced.

FIG. 4 Additional plasmids used for targeting the human c gamma 1 sequences. Plasmids shown in FIG. 4A and 4B are the same as described for the plasmid shown in FIG.3 except: both plasmids shown in FIG. 4A and 4B have the 500 bp Bgl II/Pvu II containing the SV40 enhancer and promoter from pSV2neo (J. Molec. Appl. Genet. I:327-341, 1982) in place of the CMV promoter and enhancer, and plasmid 4B has the 7 kb Hind III/Bam HI fragment encoding human c gamma 1 with more sequence downstream of the constant region exons.

5. DETAILED DESCRIPTION OF THE INVENTION

The present invention is directed to a process for producing chimeric antibodies using novel recombinant DNA vectors to direct a desired sequence alteration to a specific location within the genome via homologous recombination in vivo. Using the method of the invention, the protein sequence of an antibody molecule can be modified by transfection of the antibody producing cell line with an appropriate "target vector." In one embodiment of the invention, a cell line that produces an antibody molecule having a desired antigen specificity is transfected with a target vector of the invention which comprises a recombinant DNA molecule that encodes a "replacement gene" and a "target sequence." The replacement gene encodes the desired molecule which is to replace all or a portion of the constant region of the antibody molecule expressed by the cell line. For example, the replacement gene may encode all or a portion of an immunoglobulin constant region having a particular effector function, class and/or origin, including but not limited to IgG, IgA, IgM, IgD or IgE constant regions of human or any other desired species; alternatively, the replacement gene may encode another type of molecule which may confer some other function to the resultant chimeric antibody; e.g., an enzyme, toxin, a biologically active peptide, growth factor, inhibitor, conjugatable peptide linker, etc. The target sequence of the target vector is homologous to DNA sequences found in the chromosome within or adjacent to the mature gene coding sequence for the constant region of the immunoglobulin produced by the cell line to be transfected or an appropriate portion of the mature coding sequence for the constant region. After transfection, homologous recombination within the antibody producing cell line will occur; some of these recombination events will lead to the replacement of all or a portion of the constant region of the immunoglobulin gene with the replacement gene, and, therefore, the expression of chimeric antibody molecules by the transfected cells.

In an alternate embodiment of the invention, a cell line which produces an antibody molecule having a desired constant region is transfected with a target vector containing a replacement gene encoding all or a portion of a variable region having a desired antigen specificity and a target sequence which directs gene modification of all or a portion of the variable coding region in the host cell chromosome. After transfection, homologous recombination within the antibody producing cell line will occur; some of these recombination events will lead to the replacement of all or a portion of the variable region of the immunoglobulin gene with the replacement gene and, therefore, the expression of chimeric antibody molecules by the transfected cells.

Once the transfectant that expresses the chimeric antibody is identified, the practice of the invention involves culturing the transfectant and isolating the chimeric antibody molecules from the cell culture supernatant using techniques well known in the art for isolating monoclonal antibodies. Alternatively, the transfected cells may be cultured in ascites fluid in animals and harvested using well known techniques for isolating monoclonal antibodies.

The various aspects of the invention are described in more detail in the subsections below and demonstrated by way of examples in which mouse/human chimeric immunoglobulin heavy chains are produced. For purposes of clarity in discussion the invention will be described as follows: (a) the target vectors; (b) transfection; and (c) screening and selection of transfectants which produce chimeric antibody molecules.

5.1. Target Vectors

As explained previously, the target vectors of the invention comprise recombinant DNA vectors including, but not limited to, plasmids, phages, phagemids, cosmids, viruses and the like which contain the replacement gene and the target sequence. As described in more detail below, the replacement gene may comprise any of a number of genes that encode a desired structural product whereas the target sequence may vary depending upon the type of antibody molecule being converted and the animal cell-type being transfected. The target sequence and the replacement gene are positioned in the target vector so that transfection of the appropriate antibody-producing cell line with the target vector results in targeted homologous recombination so that gene conversion is accomplished by site specific insertion of the replacement gene into the antibody gene.

The target vectors of the invention may contain additional genes which encode selectable markers; e.g., drug resistance, enzyme, to assist in the screening and selection of transfectants or may be co-transfected with such markers. Other sequences which may enhance the occurrence of recombinational events may be included as well. Such genes may include but are not limited to either eucaryotic or procaryotic recombination enzymes such as REC A, topoisomerase, REC 1 or other DNA sequences which enhance recombination such as CHI. Various proteins, such as those encoded by the aforementioned genes may also be transfected in order to increase recombination frequencies. Various target sequences, replacement genes, and selectable markers which may be used in accordance with the method of the invention are described below.

5.1.1. Target Sequence

The composition of the target sequence may vary depending upon whether the target plasmid is to be used to replace all or a portion of either the variable or constant region genes of light chains or heavy chains and, further, upon the animal species of the antibody-producing host cell. More specifically, target sequences should be homologous to sequences which are adjacent to or which flank the coding region for the constant or variable region, or the portion thereof, to be replaced or altered.

For example, in a chromosome, mature heavy chain genes are comprised, at their 5'termini, of the VDJ regions; i.e., the variable region (V), diversity region (D), and joining region (J) followed by any remaining J regions which are not expressed (the number of J regions varies with the species), and intronic sequences. The central and 3'portion of the gene consists of the constant region exons (flanked and interspersed with intronic and untranslated sequences) which may be one of various classes (e.g., mu, delta, gamma, epsilon, alpha) each of which is associated with its own adjacent switch region. Thus, the target sequence used to target homologous recombination in the heavy chain gene of an antibody producing host cell may comprise a region that is homologous to any portion of the antibody gene, depending on the desired alteration. For example, the target sequence for directing replacement of heavy chain constant regions may comprise sequences homologous to sequences spanning any region up to and including or excluding the switch region commencing with V, D or J and would be positioned accordingly in the construction of the target vector; e.g., at a location 5'to the coding region of the replacement gene. The actual target sequence that could be used may vary depending upon the animal species of the target host cell and the class of antibody expressed by the target host cell.

By contrast to the arrangement of heavy chain genes in a chromosome, the mature light chain genes are composed of a VJ region at their 5'termini, intronic sequences, and a single constant region exon. Thus, the target sequence used to target homologous recombination in the light chain gene of an antibody producing host cell may comprise a region that is homologous to any portion of the gene, depending on the desired alteration. For example, the target sequence for directing the replacement of light chain constant regions may be homologous to sequences spanning all or portions of the appropriate V and J through intronic sequences preceding the coding region for the constant region of the light chain. Such target sequences would be appropriately positioned in the target plasmid; e.g., at a location 5'to the coding sequence for the replacement gene. Once again, the actual nucleotide sequence of the target sequence may vary with respect to the animal species of the target host antibody producing cell.

In addition to the sequences described above, the target sequence may include sequences homologous to regions adjacent to the 5'and/or 3'terminus of the coding region for the constant heavy or light chain, and therefore, would be positioned accordingly in the construction of the target vector; i.e., at a location 5'and/or 3', respectively, to the coding region of the replacement gene. In a similar fashion, target sequences for directing the replacement of heavy or light chain variable regions may comprise sequences homologous to all or portions of the appropriate regions that flank the variable region. In any case, target sequences may also include coding region sequences flanking an area within an exon where only a portion of the variable or constant region is to be replaced so that the protein expressed is altered in a desired fashion.

5.1.2. Replacement Gene

As previously explained, the replacement genes used to convert antibody constant regions may comprise the coding sequence for all or a portion of a constant region of an immunoglobulin of a different class and/or animal or human species. Thus, in the case of heavy chains, the replacement gene may comprise all or a portion of the gene encoding the constant regions of human IgM, IgD, IgG, IgE, and IgA, or any subclass thereof. Alternatively, the replacement gene may encode a product which can confer some different effector function to the chimeric molecule which would be expressed. For example, an enzyme, toxin, growth factor, biologically active peptide, linker, etc. The replacement gene may also consist of any combination of aforementioned sequences, for example, all or a portion of an antibody constant region linked to a novel protein sequence.

The replacement gene chosen depends, in part, upon the use intended for the chimeric antibody molecule expressed. For example, if therapeutic use in humans is intended, then the replacement gene could encode a human constant region, preferrably of a class having a desired effector function for the therapeutic use in mind. If an improvement or alteration in the existing effector function of the antibody is desired, a portion of the constant region may be replaced with a sequence that confers such improved or altered effector function to the resulting chimeric antibody molecule. If targeted delivery of an enzyme, toxin, drug, hormone or growth factor in vivo is desired, a replacement gene encoding the enzyme, toxin, drug, hormone or growth factor or an appropriate linker for conjugation to such should be used. If the chimeric antibodies are to be used in diagnostic assays, for example where labeled antibodies are utilized, a replacement gene encoding an enzyme or its substrate could be used. Such enzymes/substrate system include, but are not limited to those which produce a colored product when reacted; for example, betagalactosidase, alkaline phosphatase, horseradish peroxidase, and the like. The resulting chimeric antibodies may be used as labeled antibodies in the procedures intended with or without further modification, e.g., the chemical attachment of enzymes, drugs, toxins, hormones, growth factors etc.

The replacement gene used to convert antibody variable regions may comprise all or a portion of the coding sequence for a variable region of an antibody molecule that defines a desired antigen. These may encode antigen binding regions that define related or completely unrelated antigens. If an improvement or alteration in antigen binding or specificity, is desired, a portion of the variable region may be replaced with a sequence that confers such improved or altered binding or specificity to the resulting chimeric antibody molecule.

5. 1. 3. Selectable Marker and Other Elements

In addition to the target sequence and the replacement gene, the target vector of the invention may encode a selectable marker which assists in the screening and selection of antibody producing cells that have been successfully transformed. Such markers include drug resistance genes, such as gpt, neo, his, etc., and the like.

Additional elements which may enhance the number of recombinational events may be included in the target vector. For example, an origin of replication (ori) that is temperature sensitive (for example polyoma tsA ori system) may be included in the construct so that growth of 0 transfectants at a permissive temperature results in vector replication so that the copy number of target sequence and replacement gene is increased, and the subsequent number of recombinations may be increased. Other ori systems could also be utilized to increase copy number (e.g., EBV ori plus 5 factors, BPV ori plus factors, or SV40 ori and T antigen).

5.2. Transfection of Antibody-Producing Cell Lines with Target Vectors

In accordance with the method of the invention, a cell line which produces a desired antibody (i =., one having a desired antigen specificity or a desired constant region) is transfected with the appropriate target vector to produce transfectants that will undergo site directed homologous recombination. Both light chain and heavy chain target vectors can be used to transfect an appropriate antibody producing cell line; however, in many cases transfection with a heavy chain target vector may be sufficient to obtain expression of a chimeric antibody molecule.

Transfection may be accomplished by any of a number of methods known to those skilled in the art, including, but not limited to calcium phosphate precipitation, electroporation, microinjection, liposome fusion, RBC ghost fusion, protoplast fusion, etc. The target vector may be linearized by cleavage with a restriction enzyme within the target sequence prior to transfection in order to increase the probability of homologous recombination in the transfected cell.

5.3. Screening and Selection of Recombinants

The ultimate test for successful transformation, homologous recombination and targeted gene modification is the production of chimeric antibodies by the antibody producing cell line. The detection of transfectants which produce chimeric antibodies can be accomplished in a number of ways, depending upon the nature of the replacement gene product.

If the target vector contains a selectable marker, the initial screening of transfected cells should be to select those which express the marker. For example, when using a drug resistance gene, those transfectants which grow in the selection media containing the otherwise lethal drug can be identified in the initial screening. A second screening would then be required to identify those transfectants which express the chimeric antibody.

The protocol for the second screening depends upon the nature of the replacement gene. For example, the expression of a replacement gene that encodes the constant region of a different antibody class or species can be detected by an immunoassay using antibodies specific for the particular immunoglobulin class and/or species; alternatively, a bioassay could be performed to test for a particular effector function conferred by the replacement gene. The expression of a replacement gene which encodes a biologically active molecule such as an enzyme, toxin, growth factor, or other peptide could be assayed for the particular biological activity; for example, the transfected cell products can be tested using the appropriate enzyme substrate, or target for the toxin, growth factor, hormone, etc; alternatively, these replacement gene products could also be assayed immunologically using antibodies which are specific for the replacement gene product.

The transfectants which express a replacement gene should also be tested for appropriate antigen recognition. This can be accomplished by an appropriate immunoassay, including a competitive immunoassay using the original and chimeric antibodies. These screening tests need not be carried out sequentially and, in fact, could be conducted simultaneously using a "sandwich immunoassay" in which a capture antibody that defines the replacement gene product (i.e., either the constant or variable region) is used to immobilize the chimeric antibody and the presence or absence of the unaltered portion (i.e., either the unaltered variable region or unaltered constant region, respectively) is detected (i.e., using labeled antigen or labeled antibody, respectively). For example, the antigen could be used to capture the chimeric antibodies and the constant region replacement gene product could be detected using labeled antibodies that define the replacement gene product, or by assaying the captured chimeric antibodies for the biological activity of the replacement gene product (e.g., enzymatic, toxin, hormone, growth factor, etc.). Alternatively, the chimeric antibody can be immobilized at the constant region (e.g., using an antibody specific for that region, or staphylococcal A protein, etc.) and the variable region gene product could be detected using labeled antigen or an anti-idiotype antibody.

6. Example: Replacement of the Constant Region of a Murine Immunoglobulin Heavy Chain with the Constant Region of Human Gamma 1 Immunoglobulin The examples that follow describe the construction of a target plasmid containing a murine target sequence (encoding the fourth joining region and enhancer of the heavy chain gene) ligated to a replacement gene encoding the constant region of a human gamma 1 immunoglobulin (huIgG1). This target plasmid was used along with a phage containing the entire mature gene encoding a murine heavy chain (the entire variable and constant region) to co-transfect murine myeloma cells which are heavy chain mutants that ordinarily express only light chains. The transfected cells were screened and clones expressing the human IgG1 heavy chain were identified. These experiments indicate the successful homologous recombination event, integration into the host cell chromosomes, and expression of the human gamma 1 gene in a murine cell system.

6.1. Materials and Methods

Unless otherwise indicated, the materials and methods indicated below were used in the examples that follow. cl 6.1.1. Transfection The transfections were carried out by washing and resuspending about $10^7$ cells in PBS (phosphate buffered saline) at 4.C with 2 mM MglC$_2$ and 2 mM CaCl$_2$, and transferring the cells to a sterile plastic cuvette lined with aluminum foil (BioRad, CA). The linearized DNA was added and mixed at a final concentration of 10–100 ug/ml, then an electrical charge was applied with an appropriate power supply (e.g., a Gene Pulsar, BioRad, CA). The cuvettes were gently "flicked" to insure good mixing. After 2 minutes at room temperature the cells were then transferred to 9 ml of RPMI media (GIBCO) with 10% FBS at 37° C. After 48 hours incubation, viable cells were recovered by centrifugation, counted, and plated out at a density of $10^3$ cells/well in 96 well plates or at $10^4$ cells per well in 24 well plates in RPMI media with 10% FBS, penicillin (60 mg/ml)/ streptomycin (100 mg/ml), sodium pyruvate (1 mM), L-glutamine (292 mg/ml), and 0.1–2 ug/ml mycophenolic acid or 1–2 mg/ml G418. The same media was either replenished or exchanged every 2 to 3 days. After 2 to 3 weeks, wells were scored for growth. Supernatants from cultures were then assayed by ELISA for the presence of human gamma 1 and positive wells were cloned and screened again.

6.1.2. Screening Transfectants For Successful Recombinants

ELISA assays were performed by coating immulon 2 plates (Dynatec Labs, Chantilly, VA) with 100 ul of either goat anti-human IgG (Antibodies Inc., Davis, CA) at a 1:1000 dilution, or goat anti-mouse IgA (Cappel) at a 1:5000 dilution in coating buffer (0.1 M NaHCO$_3$ pH 9.6) at 4° C. overnight. Plates were then filled with specimen diluent (Genetic Systems) to block for one hour at room temperature after which they were shaken out, sealed, and stored at 4° for no more than 3 weeks. The plates were readied for assay by washing 3 times with wash buffer (0.15 M NaCl, 0.05% v/v Tween 20) and then 100 ul of standards (diluted in the appropriate media) or culture supernatants were added and incubated at 37.C for 1 hour. The plates were then washed 3 times with wash buffer and bound antibody was detected with 00 ul of either horseradish peroxidase (HRP) conjugated goat anti-human IgG (American Qualex) at a 1:6000 dilution, HRP goat anti-mouse IgA (Cappel) at a 1:5000 dilution, or HRP goat anti-mouse Lambda (Southern Biotech. Ass. Inc., Birmingham, AL) at a 1:3000 dilution, for 1 hour at 37.C. Plates were then washed 3 times with wash buffer and incubated at room temperature for 15 minutes with a 1:100 dilution of TMB Chromogen in buffered substrate (Genetic Systems), stopped with 100 ul per well of 3M H$_2$SO$_4$, and read immediately at 450/630 nm on a micro plate reader (Genetic Systems). Likewise, Kappa producing cell lines can be screened using an HRP goat anti-mouse Kappa reagent (Southern Biotech. Ass. Inc.). Cell lines positive for human IgG and/or murine IgA were subcloned by limiting dilution or in soft agarose to isolate expressing clones. To clone in soft agarose, approximately 1000 cells from a positive well were resuspended in 0.4% agarose and layered over an agar layer of murine peritoneal exudate feeder cells. A third layer containing antiserum specific for human IgG1 was overlayed 1 to 2 days later. Positive clones were identified by the presence of an immunoprecipitate.

6.1.3. Southern and Western Blots

High molecular weight DNA was isolated from cells essentially as originally described by Blin and Stafford (Blin. N. and Stafford, D.W., 1976, Nucleic Acids Res. 3:2303) and later by Maniatis, Fritsch and Sambrook (Maniatis et al., 1982, Molecular Cloning—A Laboratory Manual, Cold Spring Harbor, NY p. 280) with the exception that the cells were first washed in standard phosphate buffered saline (as opposed to Tris) and the RNase treatment was carried out simultaneously with the proteinase K treatment at 55° C.

Southern blots and hybridization were performed as originally described by Southern (Southern, 1975, J. Mol. Biol. 98:503) and more recently detailed by Maniatis, Fritsch, and Sambrook (Maniatis et al., 1982, Molecular Cloning—A Laboratory Manual, Cold Spring Harbor, NY, pp. 383-389). Probes used for hybridization were the 1.0 kb Hind III-PstI fragment containing the first constant region domain of the human IgGI gene, or the 0.7 kb Hind III-Hind III fragment encoding the murine $J_{H2}$ and $J_{H3}$ gene segments. Labeling of probes was performed as per the manufacturers protocol using a Nick Translation Kit (Bethesda Research Laboratories). Restriction enzymes were purchased from Boehringer Mannheim Biochemicals.

Western blot analysis was performed as described (Towbin et al., 1979, Proc. Natl. Acad. Sci. (USA) 76:4350) and the developing reagents are the same as those used for detection in the ELISA assay.

Figure 1:
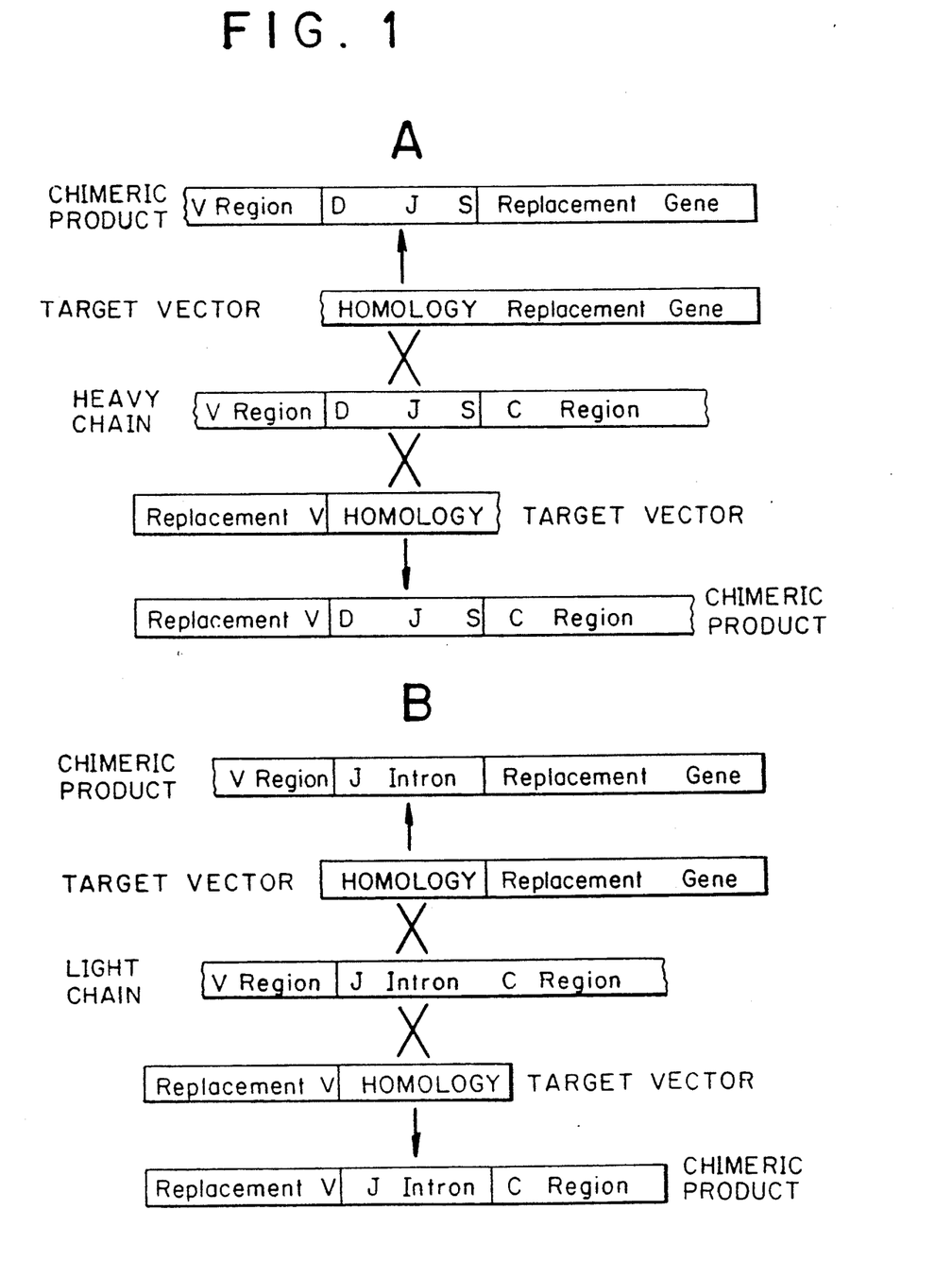
Figure 2:
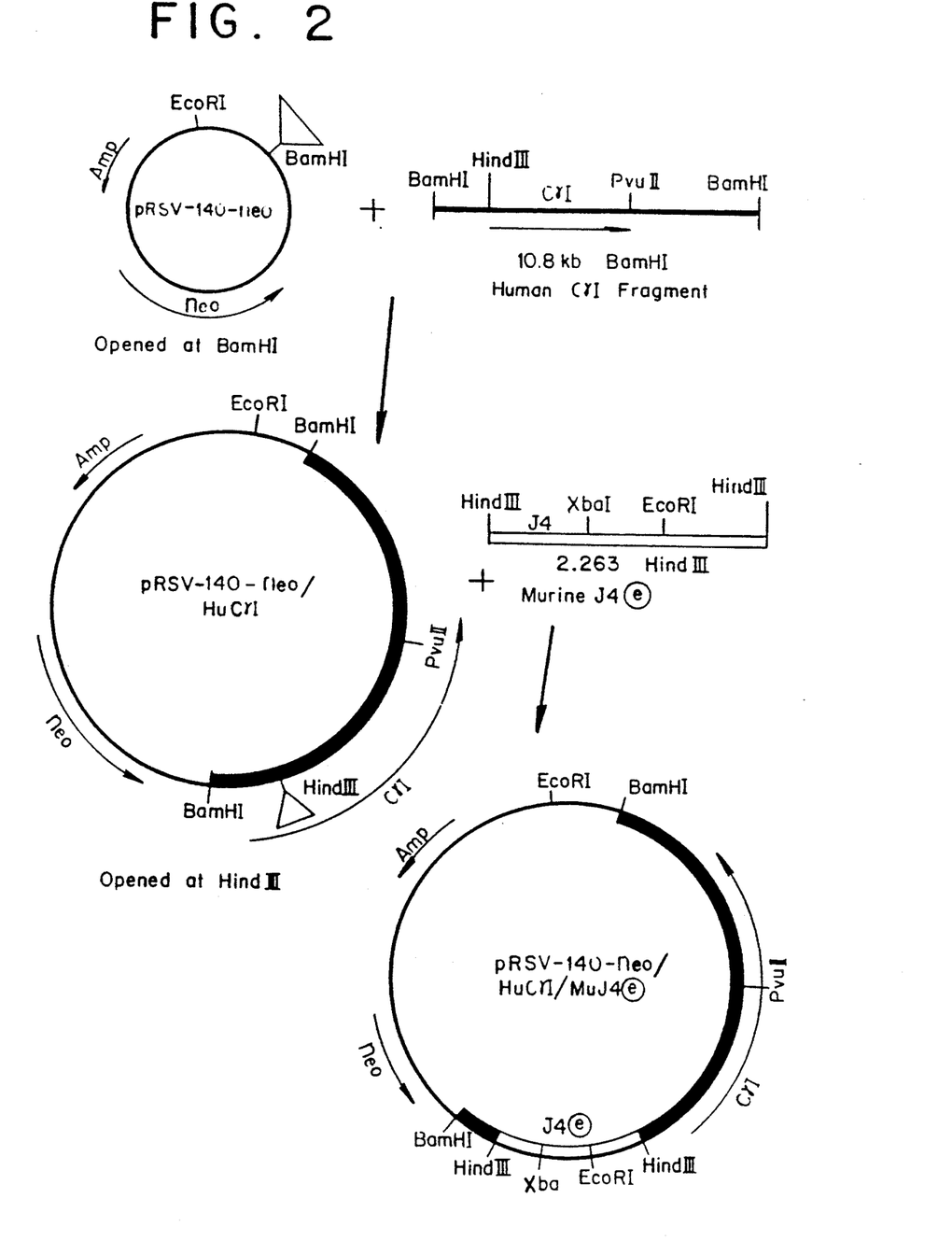
FIG. 2 diagrammatically represents the construction of a target plasmid pRSV-140-neo/HuC-gamma 1/MuJ4/e. The target sequence comprises a 2.2 kb Hind III fragment derived from the murine immunoglobulin heavy chain (IgH) locus which contains the fourth joining region (J4), the IgH enhancer (e) and intronic sequences 5′to the switch region. The target sequence is positioned 5′to the replacement gene which comprises a 7.0 kb Hind III-Bam HI fragment of the human IgG1 heavy chain locus containing the human gamma 1 constant region.

6.2. Construction of Target Plasmids Encoding Human Immunoglobulin Constant Region A target plasmid was constructed which consists of the bacterial plasmid vector pRSV-140-neo into which a 8.0 kb Hind III- Bam HI fragment containing the human gamma 1 constant region gene was cloned as the replacement gene (FIG. 2). The target gene, a 2.2 kb Hind III fragment derived from the murine immunoglobulin heavy chain (IgH) locus which contains the fourth joining region (J4), the IgH 0 enhancer (e) and intronic sequences 5'to the switch region, was inserted into the Hind III site located 5' to the human gamma 1 gene (FIG. 2). This construct was then linearized at the unique Xba I site within the murine target sequence and transfected into the murine myeloma cell line described below by means of electroporation previously decribed.

6.3. Transfection and Homologous Recombination

The experiments and results described below demonstrate successful homologous recombination between the target plasmid and the murine heavy chain gene contained within the phage which was used to co-transfect a murine myeloma host cell. Homologous recombination and integration into the murine myeloma host cell chromosome resulted in the expression of a human immunoglobulin heavy chain (IgG1).

6.3.1. Co-Transfection of Murine Myeloma Cells

The target plasmid containing (a) the murine target sequence encoding the fourth joining region (J4) the IgH enhancer, and intronic sequences 5'to the switch region, and (b) the replacement gene encoding the human IgG1 constant region, was linearized in the region of the target sequence and co-transfected at an equimolar ratio with a phage DNA clone containing the functional J558 murine heavy chain gene, into the heavy chain mutant mouse myeloma cell line, J558L which expresses only light chains. Transfected cell lines resistant to G418 (the selectable marker encoded by the target plasmid construct) were then screened for the presence of human IgG1 protein. Since the human gamma 1 constant region contained in the target plasmids constructed above lacks the immunoglobulin promoter sequence, the detection of expression of human IgG protein by the transfected mouse cell line should be the result of an homologous recombination event between the transfected DNA molecules and integration within the host cell chromosome.

6.3.2. Identification of Cells Secreting Chimeric Immunoglobulins

Transfectants secreting human IgG and/or murine IgA protein were subcloned. Confirmation of the homologous recombination events was provided by DNA blot transfer analysis, in which a newly rearranged restriction fragment was identified; this fragment was of the size expected (a 10.5 Kb Bam HI fragment) and contained both human gamma 1, and mouse $J_{H2}$-$J_{H3}$ sequences. Additional confirmation was obtained by Western blot analysis of supernatant proteins a protein chain of about 50 kilodaltons which demonstrated (50 kd) bearing human IgG serologic determinants present in the transfectoma culture supernatants. The antihuman IgG reagent did not react with murine IgA, which was also distinguishable based on slower electrophoretic mobility.

ELISA results also revealed the presence of murine IgA in many transfectoma supernatants. This is the result of functional J558 heavy chain gene integrating undisrupted (i.e., without undergoing an homologous recombination event). By comparing the level of human IgG and mouse IgA expression and production, the frequency of homologous versus nonhomologous recombination events has been estimated to be between 30-80%, depending on the experiment.

The results presented above have conclusively demonstrated: (a) that the target plasmid works as designed; and (b) that myeloma cells are very efficient in their ability to mediate homologous recombination.

Sequences homologous to regions upstream and/or downstream of variable region gene segments could be used in conjunction with variable region gene segments or portions thereof to alter the antigen affinity and/or specificity. Moreover, the J558 system described herein can be used as a screening procedure for identifying recombination enhancing proteins.

7. Example: Production of Chimeric Immunoglobulin Heavy Chain with Specificity to L20 Human Tumor Associated Antigen The experiments described below demonstrate that murine hybridoma cells can efficiently mediate homologous recombination and that this capability can be exploited to direct major reconstructions of the endogenous immunoglobulin heavy chain locus. A plasmid was constructed containing the human IgG1 constant region exons flanked by the murine heavy chain enhancer and the neomycin gene. This construct was used to direct the production of antigen specific chimeric heavy chain Ig by site specific targeting to the endogenous heavy chain locus of the hybridoma cell line L20 which produces a monoclonal antibody specific for a human tumor associated antigen (Patent application no. 834,172, filed Feb. 26, 1986 and references incorporated therein). The frequency of the targeting event is observed to be 1 in 200 or 0.5% of the hybridoma cells which integrate the plasmid.

7.1. Construction of Target Vector and Transfection of Hybridoma L20

Figure 3:
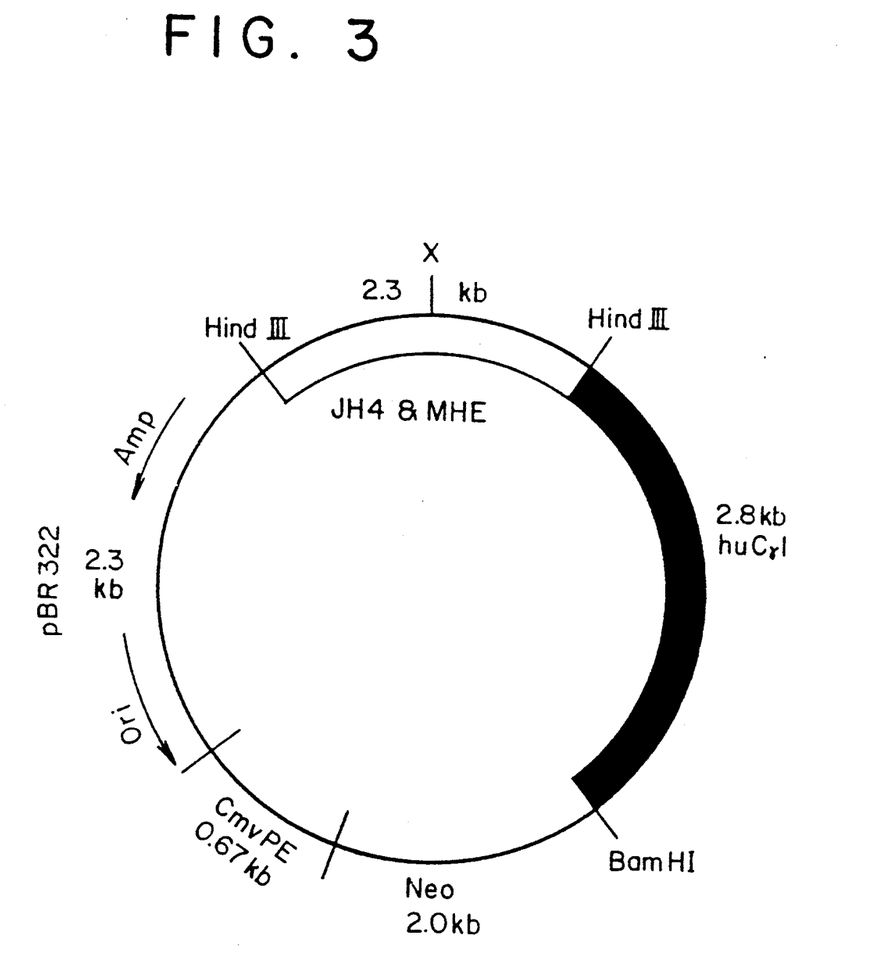
FIG. 3 Map of human IgG1 recombination vector. The vector is comprised of a 2.2 kb Hind III fragment containing the murine heavy chain enhancer which has been modified to remove an Xba I site, a 3.0 kb Hind III/Pvu II fragment containing the constant region exons of human gamma 1 (huCγ1), the 2.0 kb Bgl II/Bam HI fragment derived from pSV2/neo which encodes neo, a 667 bp Bal I/Sst I fragment bearing the human CMV enhancer and promoter, and a 2.3 kb Pvu II/Hind III fragment from pBR322 which includes the origin of replication and the ampicillin resistance gene. The Bal I/Sst I fragment containing CMV was transferred into the Sst I/Hinc III sites of pEMBL 18, removed as a Hind III/Sst I fragment and cloned between the same sites in Pic19R, then isolated as a Sma I/Bgl II fragment to place between the Pvu II and Bgl II sites in the construct. Similarly, the Hind III/Pvu II fragment bearing the human c gamma 1 exons was cloned into the Hind III and Hinc II sites of Puc 9, then transferred as a Hind III/Bam HI fragment.

A plasmid vector was constructed which contains the constant region exons of human IgG1 (Cg1) flanked by the murine heavy chain enhancer (MHE), and the neomycin resistance gene (NEO) (FIG. 3). The plasmid was linearized at a unique Xba I site within the 2.2 kb region of sequence identity shared with the murine IgH locus, and transfected into the hybridoma cell line L20 which produces a murine IgG1 antibody specific for an antigen expressed primarily on human carcinoma cells as follows: The vector described in FIG. 3 was linearized at the unique Xba I site and 50 ug was used to transfect $8 \times 10^6$ L20 hybridoma cells by. electroporation (as previously described in materials and methods). Viable cells were plated at a density of $1 \times 10^4$ (or $1 \times 10^3$ for frequency calculation) cells/well in 96 well plates in IMDM 10% FBS media containing 2.5 mg/ml G418. The plates were fed every 2-3 days and after 2 weeks all wells were screened for the production of human IgG1 using standard ELISA techniques. Goat anti-human IgG (Cat. #4132 Antibodies Inc., Davis CA) at a 1:10,000 dilution was used as a capture reagent, and goat anti-human IgG/HRP (Cat #HAP009 American Qualex, La Mirada CA) at a 1:6000 dilution was used to detect. All positive supernatants were verified in subsequent ELISAs as well.

Since the human IgG1 exons are not associated with a variable region gene segment, production of human IgG1 heavy chain protein can only occur by recombination of the plasmid with a functional promoter, initiation codon, and splicing sequences. Thus, cells surviving selection in G418 containing media (i.e., all those which satisfactorily ; integrated the plasmid) were assayed for production of human IgG1 by ELISA (Table I).

TABLE I

| FREQUENCY OF INTEGRATION EVENTS WHICH RESULT IN HUMAN IgG1 PRODUCTION | | | | |
|---|---|---|---|---|
| INT EVENTS PER WELL | WELLS SCREENED | TOTAL EVENTS | WELLS W/HU IgG1 | FREQ |
| 2.2 | 480 | 1056 | 8 | 0.75% |

The frequency of transfection was determined by plating at lower density, and the frequency of integration events resulting in production of human IgG1 was therefore observed to be on the order of 1 in 132 or 0.75%. More recent experiments with the same cells and plasmid resulted in the production of human IgG in 2 of 512 integrations, or 0.39% - these suggest that an average frequency may be closer to 0.5%. Interestingly, even after cloning, most cell lines were found to produce both murine and human IgGl, although occasional clones were isolated which produced one or the other (Table II). Cells from parent wells producing human IgGl were plated at limiting dilution and 12 clones from each parent were assayed for production of human IgGl (huIgGl) (as described for Table 1) and mouse IgG. Mouse IgG (mIgG) assays were carried out using goat anti-mouse IgG (Cat #1070 Southern Biotech, Birmingham AL) and goat antimouse Kappa/HRP (Cat #OBI141-85 Fisher Biotech, Orangeburg NY) as capture and detecting reagents respectively. Results are shown in Table II. Numbers given are of clones producing human antibody, mouse, or both.

TABLE II

| PRODUCTION OF MOUSE vs HUMAN IgG1 IN CLONES FROM L20 TRANSFECTANTS PRODUCING HUMAN IgG1 | | | |
|---|---|---|---|
| PARENT | huIgG1 | mIgG | huIgG1/mIgG |
| 7C5 | 0 | 0 | 12 |
| 7E6 | 1 | 0 | 11 |
| 8D6 | 0 | 0 | 12 |
| 8F8 | 2 | 2 | 8 |
| 8H12 | 1 | 0 | 11 |
| 10G3 | 0 | 2 | 10 |
| 9F11 | 0 | 1 | 11 |
| 9F12 | 1 | 0 | 11 |

7.2. Characterization of Expressed Chimeric L20 Heavy Chain

7.2.1. Western Blot Analysis

The human heavy chain was shown to be serologically distinct and in the expected size range by Western blot analysis of supernatants from selected clones as follows: cultures nearing the plateau portion of growth were washed and resuspended in serum free media. After 24 hours the supernatants were harvested, dialyzed vs. 0.1 M NH4OAc, lyophylized, and resuspended in 5 mM Tris, pH 6.8. Aliquots of these samples and the parent cell line L20, plus purified antibody 2H9 (a human IgGl protein), and purified murine L20 IgGl were denatured by boiling in the presence of $\beta$-mercaptoethanol and electrophoresed through a gradient acrylamide gel ranging between 10 to 20%. The gel was transferred to nitrocellulose paper electrophoretically. The resulting filter was blocked with 2% nonfat dry milk in PBS, stained with goat anti-human IgG/HRP (#10501 CALTAG, San Francisco CA) and developed with 30 mg 4-chloro-1 napthol (Sigma, St. Louis MO) in Tris buffered saline.

7.2.2. Flow Cytometric Analysis

Both the human and murine IgGl were also demonstrated to be antigen specific by flow cytometry (Table III) as follows: The samples used for western blotting were assayed by ELISA to determine the concentration of murine and human IgGl. Dilutions were made to adjust the concentrations (in ug/ml) to those given for flow cytometry analysis. Five $\times 10^5$ cells from the human tumor lines 2981 or 3347 (Hellstrom et al., 1986, Proc. Natl. Acad. Sci. USA 83:7059-7063) were incubated in the presence of the L20 antibodies indicated (or media) for 30 minutes at 4° C., washed 2×, and stained with a 1:50 dilution (in media) of either goat anti-human IgG/FITC (fluorescein isothiocyanate) (CALTAG, San Francisco CA) or goat anti-mouse IgG/FITC (TAGO, Burlingame CA—heavy and light chain specific) for 30 minutes at 4° C. These preparations were then washed twice, resuspended, and analyzed by flow cytometry for relative fluorescence. Results are shown in Table III. The values given are the linear fluorescence equivalence (LFE) of each preparation.

TABLE III

| ANTIGEN SPECIFICITY OF MURINE AND HEAVY CHAIN CHIMERIC L20 ANTIBODIES | | | | |
|---|---|---|---|---|
| | Ab conc | | LFE | |
| CLONE | huIgG | mIgG | α-hu | α-m |
| | | | 2981 Target | |
| 7E6-10 | 1.0 | 0 | 35 | 6 |
| 8H12-8 | 1.0 | 0 | 38 | 7 |
| 8F8-8 | 1.0 | 0.5 | 39 | 11 |
| 9H12-1 | 1.0 | 0.1 | 42 | 7 |
| 8F8-10 | 0 | 0.4 | 2 | 10 |
| 10G3-5 | 0 | 1.0 | 2 | 31 |
| mL20 | 0 | 1.0 | 2 | 18 |
| media | 0 | 0 | 2 | 2 |
| | | | 3347 Target | |
| 7E6-10 | 0.4 | 0 | 7 | 3 |
| mL20 | 0 | 0.4 | 2 | 3 |
| media | 0 | 0 | 2 | 2 |

Thus, the parental L20 cell line most probably retains two copies of the productive heavy chain allele, only one of which undergoes a specific recombination within a given cell. The production levels for clones expressing only the chimeric antibody was found to be on the order of 5-10 ug/ml in 10 ml culture supernatants at the plateau phase of growth.

7.2.3. Southern Blot Analysis

Southern blot analysis using a probe specific for human Cγ1 demonstrated integration specific fragments in common between all cell lines producing human IgGl with three different enzymes. A Bam HI site was mapped 1.4 kb upstream of the target sequence in the L20 parental line, therefore an insertion of the recombination vector at the target site is expected to produce a Bam HI fragment of 5.5 kb which hybridizes to a huCγ1 probe. Such a fragment was observed in each clone producing human IgGl.

7.2.4. ADCC Analysis

The murine L20 IgGl antibody was compared with the protein bearing the chimeric heavy chain for activity in an ADCC assay (Hellstrom et al., 1985, Proc. Natl. Acad. Sci. USA 82:1499-1502). As can be seen from the results in Table IV, changing the heavy chain constant regions to those of human IgGl provides a novel effector function to this specificity.

TABLE IV

| ADCC OF 2981 TARGET CELLS MEDIATED BY MURINE MAb L20 AND CHIMERIC HEAVY CHAIN L20 | | |
|---|---|---|
| Immunoglobulin | Conc (μg/ml) | ADCC of 2981 Target Cells |
| L20 8F8-8 | 4 | 58% |
| L20 7E6-10 | 8 | 53% |
| MAb L20 | 10 | 31% |
| None* | 0 | 31% |

*Effector cells (lymphocytes) only.

7.3. Chimeric L20 Heavy Chain Produced Using a Different Target Vector

Figure 4A:
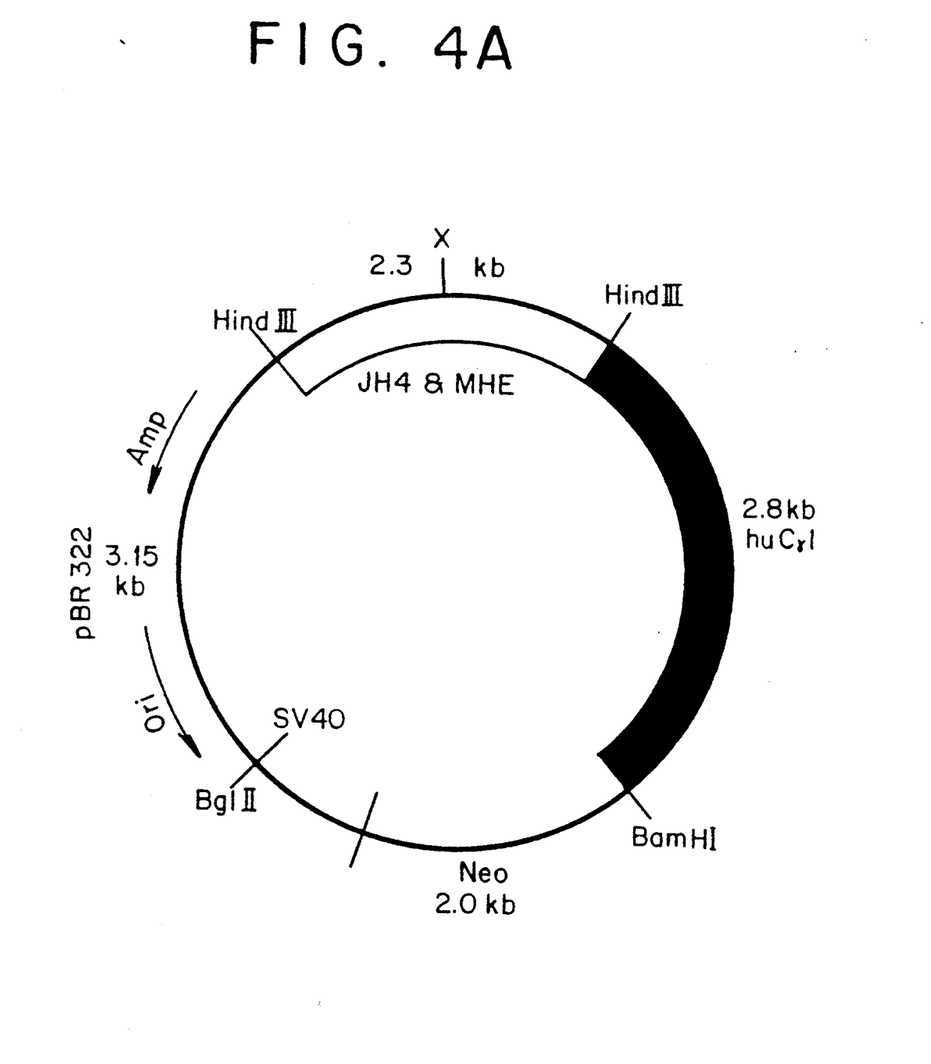

In further examples we have used another plasmid, depicted in FIG. 4A to introduce the human Cγ1 exons into murine hybridoma cells L20 resulting in the production of human IgGl chimeric heavy chain proteins.

Plasmid 4A was transfected into hybridoma cell line L20 resulting in 4 wells producing huIgG in an ELISA assay of approximately 700 integration events.

8. Construction of Chimeric G28.1 Heavy Chains

In another example we have used the plasmid shown in FIG. 3 to convert the murine hybridoma cell line G28.1 (Ledbetter et al., Leukocyte typing III, A. J. McMichael, ed., Oxford Univ. Press pp.339–340 (1987)) to the production of antigen specific human IgG1 heavy chain by the same method. A single experiment resulted in 4 huIgG1 producers out of 864 integration events. These cell lines were identified by ELISA, verified, and then tested for their ability to bind to tonsilar B cells as follows: human tonsilar B cells were incubated with supernatant from the cell lines indicated (or Media), washed and counterstained with either goat anti-human IgG ($\alpha$ hu) or goat anti-mouse IgG ($\alpha$ m) as previously described, and analyzed by flow cytometry. Results are shown in Table V. The supernatants were quantitated by ELISA for mouse and human IgG and values are given in ng/ml. Fluorescence data are expressed as linear fluorescence equivalents.

TABLE V
ANTIGEN SPECIFICITY OF HEAVY CHAIN CHIMERIC G28.1 SUPERNATANTS

| CELL LINE | huIgG | mIgG | LFE |
|---|---|---|---|
| | | | $\alpha$-hu |
| 11F10 | 0 | 87 | 9 |
| 1F11 | 97 | 89 | 93 |
| 4F5 | 86 | 91 | 38 |
| 3D2 | 90 | 86 | 77 |
| 3D11 | 56 | 85 | 16 |
| Media | 0 | 0 | 9 |
| | | | $\alpha$-m |
| G28.1 | 0 | 83 | 53 |
| Media | 0 | 0 | 3 |

The results again demonstrate preservation of antigen specificity for an antibody molecule bearing a human IgG1 chimeric heavy chain.

9. Construction of Chimeric L6 Heavy Chains

Figure 4B:
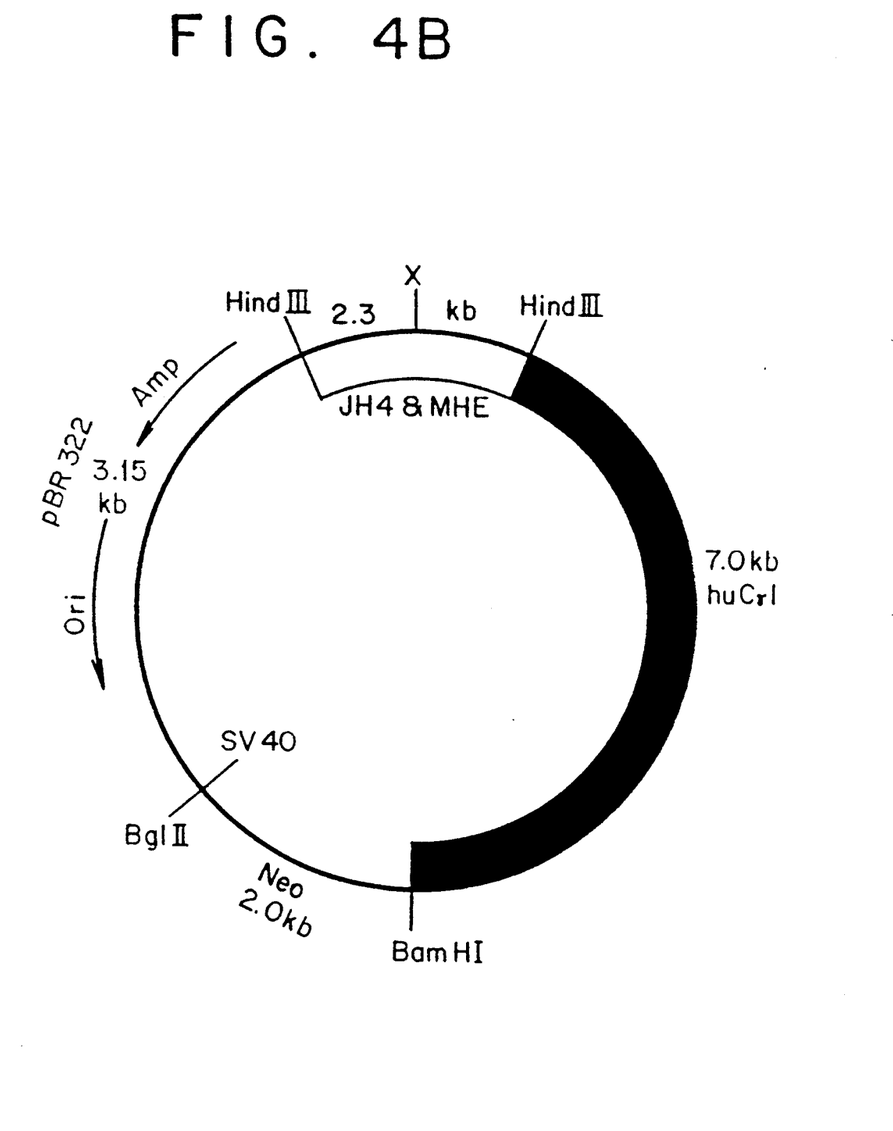

The recombinant target plasmid depicted in FIG. 4B was transfected into murine hybridoma cell line L6 resulting in a single cell line which gave rise to clones stably producing chimeric heavy chain (in the absence of murine heavy chain). The antibody was shown to bind to human tumor cells and to mediate destruction via ADCC with human effector cells more efficiently than murine L6 (Table VI), comparable to that of heavy and light chain chimeric L6 produced by conventional recombinant techniques (patent application no. 684,759, filed Dec. 21, 1984 and patent application no. 776,321, filed Oct. 18, 1985 and references incorporated therein).

TABLE VI
ADCC OF 2981 TARGET CELLS MEDIATED BY MURINE MAb L6 AND CHIMERIC HEAVY CHAIN L6

| Immunoglobulin | Conc. ($\mu$g/ml) | ADCC Of 3347 Target Cells |
|---|---|---|
| L6 7B7.16 | 0.01 | 83% |
| L6 7B7.7 | 0.01 | 82.5% |
| MAb L6 | 0.01 | 58% |
| None* | 0.01 | 53% |

*Effector cells (lymphocytes) only.

Southern blots confirmed the presence of a 10 kb Ava I fragment, and an 8 kb Bgl II fragment, both of which hybridize to a huCg1 probe. These fragments are consistent with insertion of the vector plasmid at the target site based on previous mapping of the cloned genomic L6 heavy chain variable region gene segment.

The present invention is not to be limited in scope by the embodiments disclosed in the examples which are intended as but single illustrations of different aspects of the invention and any methods which are functionally equivalent are within the scope of this invention. Indeed, various modifications of the invention in addition to those shown and described herein will become apparent to those skilled in the art from the foregoing description. Such modifications are intended to fall within the scope of the appended claims.

What is claimed:

1. A method for the production of a cell line expressing a modified antibody molecule comprising:
    (a) transfecting an antibody producing lymphoid cell line with a target vector comprising:
        (i) a replacement gene to modify a portion of the genomic sequence of the immunoglobulin genes of the lymphoid cell line, and
        (ii) a target sequence homologous to a second DNA sequence adjacent to the immunoglobulin sequence to be converted,
    so that the replacement gene modifies the immunoglobulin sequence via site specific homologous recombination with genomic chromosomal DNA in vivo; and
    (b) selecting a transfectant which produces the modified antibody molecule.

2. The method according to claim 1 in which the immunoglobulin sequence to be modified comprises a constant region gene, or a portion thereof.

3. The method according to claim 2 in which the replacement gene encodes an immunoglobulin constant region, or portion thereof, which differs from the endogenous immunoglobulin gene constant region sequences of the lymphoid cell line.

4. The method according to claim 2 in which the replacement gene encodes an enzyme, toxin, hormone, growth factor or linker.

5. The method according to claim 1 in which the immunoglobulin sequence to be modified comprises the variable region gene, or a portion thereof.

6. The method according to claim 5 in which the replacement gene encodes an immunoglobulin variable region, or portion thereof, which differs from the endogenous immunoglobulin variable region sequences of the lymphoid cell line.

7. The method according to claim 1 in which the immunoglobulin sequence to be modified comprises a heavy chain gene.

8. The method according to claim 7 in which the target sequence is homologous to V, D, J, or switch regions or introns adjacent to the heavy chain gene to be modified.

9. The method according to claim 1 in which the immunoglobulin sequence to be modified comprises a light chain gene.

10. The method according to claim 9 in which the target sequence is homologous to V, D or J regions or introns adjacent to the light chain gene to be modified.

11. A method for the production of a modified antibody molecule, comprising:
    (a) culturing a modified-antibody-producing cell line which was prepared by transfecting an antibodylymphoid-producing cell line with a target vector comprising:
  (i) a replacement gene to convert a portion of the genomic sequence of the immunoglobulin genes of the lymphoid cell line, and
  (ii) a target sequence homologous to a second DNA sequence adjacent to the immunoglobulin sequence to be converted so that the replacement gene modifies the immunoglobulin sequence via site specific homologous recombination with genomic chromosomal DNA in vivo and the modified antibody is expressed by the transfected cell line; and (b) isolating the modified antibody molecule from the culture.

12. The method according to claim 1 or 11 in which the modified antibody molecule comprises a variable region of murine origin and a constant region of human origin.

13. The method according to claim 1 or 11 in which the modified antibody molecule comprises a variable region joined to a enzyme, toxin, hormone, growth factor or linker.

14. The method according to claim 12 in which the lymphoid cell line to be transfected produces monoclonal antibody L6.

15. The method according to claim 13 in which lymphoid cell line to be transfected produces monoclonal antibody L6.

16. The method according to claim 14 in which the lymphoid cell line comprises HB 8677 as deposited with the ATCC.

17. The method according to claim 15 in which the lymphoid cell line comprises HB 8677 as deposited with the ATCC.

18. The method according to claim 22 in which the lymphoid cell line to be transfected produces monoclonal antibody L20.

19. The method according to claim 18 in which the lymphoid cell line comprises HB 8913 as deposited with the ATCC.

20. The method according to claim 13 in which the lymphoid cell line to be transfected produces monoclonal antibody L20.

21. The method according to claim 20 in which the lymphoid cell line comprises HB 8913 as deposited with the ATCC.

* * * * *